US012491323B2

(12) United States Patent
Boström

(10) Patent No.: US 12,491,323 B2
(45) Date of Patent: Dec. 9, 2025

(54) SAFETY DEVICE FOR A MEDICAMENT DELIVERY DEVICE

(71) Applicant: SHL MEDICAL AG, Zug (CH)

(72) Inventor: Anders Boström, Ingarö (SE)

(73) Assignee: SHL Medical AG, Zug (CH)

( * ) Notice: Subject to any disclaimer, the term of this patent is extended or adjusted under 35 U.S.C. 154(b) by 614 days.

(21) Appl. No.: 17/925,804

(22) PCT Filed: May 12, 2021

(86) PCT No.: PCT/EP2021/062689
§ 371 (c)(1),
(2) Date: Nov. 16, 2022

(87) PCT Pub. No.: WO2021/244829
PCT Pub. Date: Dec. 9, 2021

(65) Prior Publication Data

US 2023/0173192 A1 Jun. 8, 2023

(30) Foreign Application Priority Data

Jun. 3, 2020 (EP) .................................... 20177954

(51) Int. Cl.
*A61M 5/32* (2006.01)

(52) U.S. Cl.
CPC ................................ *A61M 5/3271* (2013.01)

(58) Field of Classification Search
CPC .. A61M 5/326; A61M 5/3271; A61M 5/3272; A61M 2005/3247; A61M 2005/3267; A61M 2005/2073
See application file for complete search history.

(56) References Cited

U.S. PATENT DOCUMENTS

| | | | | |
|---|---|---|---|---|
| 9,694,138 | B2 | 7/2017 | Ekman et al. | |
| 10,004,854 | B2 * | 6/2018 | Evans | A61M 5/326 |

(Continued)

FOREIGN PATENT DOCUMENTS

| | | | |
|---|---|---|---|
| EP | 2763730 | B1 | 5/2016 |
| EP | 3338840 | A1 | 6/2018 |

(Continued)

OTHER PUBLICATIONS

International Search Report and Written Opinion for Int. App. No. PCT/EP2021/062689, mailed Jun. 21, 2021.

*Primary Examiner* — Laura A Bouchelle
(74) *Attorney, Agent, or Firm* — McDonnell Boehnen Hulbert & Berghoff LLP

(57) ABSTRACT

A safety device for a medicament delivery device having a housing, a medicament delivery member guard in the housing being rotationally fixed and axially movable relative to the housing, a biasing element, and a rotator arranged within the housing that rotates relative to the housing between an initial unlocked position and a final locked position, wherein the medicament delivery member guard has a guide track and a stop member, the guide track has an inclined section configured to cause rotation of the rotator, where the rotator has a protrusion configured as a stop surface, where in an initial unlocked position the protrusion is arranged in the guide track and where in a final locked position the rotator is rotated with respect to the position of the medicament delivery member guard, and wherein in the final locked position the medicament delivery member guard is locked against distal movement relative to the housing.

20 Claims, 10 Drawing Sheets

(56) References Cited

U.S. PATENT DOCUMENTS

| | | | |
|---|---|---|---|
| 10,080,847 B2 | 9/2018 | Roberts et al. | |
| 2011/0118667 A1 | 5/2011 | Zaiken et al. | |
| 2013/0324934 A1 | 12/2013 | Holmqvist et al. | |
| 2015/0246182 A1 | 9/2015 | Evans et al. | |
| 2015/0273160 A1 | 10/2015 | Olson | |
| 2019/0134315 A1 | 5/2019 | Moser et al. | |

FOREIGN PATENT DOCUMENTS

| | | |
|---|---|---|
| EP | 2344223 B1 | 3/2019 |
| EP | 2588165 B1 | 6/2020 |
| WO | 2013/032389 A1 | 3/2013 |
| WO | 2018/091257 A1 | 5/2018 |

* cited by examiner

SAFETY DEVICE FOR A MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2021/062689 filed May 12, 2021, which claims priority to European Patent Application No. 20177954.3 filed Jun. 3, 2020. The entire disclosure contents of these applications are herewith incorporated by reference into the present application.

TECHNICAL FIELD

The present disclosure generally relates to safety devices for medicament delivery devices such as autoinjectors, and particularly to a safety device with a final locked position.

BACKGROUND

Medicament delivery devices such as autoinjectors often include a safety device for avoiding injury by or contamination of a medicament delivery member or damage of the medicament delivery member before, during and after a delivery of a medicament or drug contained in the medicament delivery device; see WO 2013/032389 or WO2018/091257 for an example of a medicament delivery device with a safety device.

Such safety devices work well. However, there is still room for developing more robust solutions.

SUMMARY

The present disclosure is defined by the appended claims, to which reference should now be made.

In the present disclosure, when the term "distal direction" is used, this refers to the direction pointing away from the dose delivery site during use of the medicament delivery device. When the term "distal part/end" is used, this refers to the part/end of the delivery device, or the parts/ends of the members thereof, which under use of the medicament delivery device is/are located furthest away from the dose delivery site. Correspondingly, when the term "proximal direction" is used, this refers to the direction pointing towards the dose delivery site during use of the medicament delivery device. When the term "proximal part/end" is used, this refers to the part/end of the delivery device, or the parts/ends of the members thereof, which under use of the medicament delivery device is/are located closest to the dose delivery site.

Further, the term "longitudinal", "longitudinally", "axially" or "axial" refer to a direction extending from the proximal end to the distal end, typically along the device or components thereof in the direction of the longest extension of the device and/or component.

Similarly, the terms "transverse", "transversal" and "transversally" refer to a direction generally perpendicular to the longitudinal direction.

Further, the terms "circumference", "circumferential", "circumferentially", "rotation", "rotational" and "rotationally" refer to a direction generally perpendicular to the longitudinal direction and at least partially extending around the longitudinal direction.

There is hence provided a safety device for a medicament delivery device, the safety device comprising: a housing extending in a longitudinal direction from a proximal end to a distal end relative to a longitudinal axis and in a circumferential direction relative to the longitudinal axis; a medicament delivery member guard arranged within the housing and being rotationally fixed and axially movable in relation to the housing along the longitudinal axis between a proximal position and a distal position; a biasing element arranged between a distally directed support surface of the medicament delivery member guard and a proximally directed support surface of the housing; and a rotator arranged within the housing and being rotatable in relation to the housing between an initial unlocked position and a final locked position; wherein the medicament delivery member guard comprises a guide track and a stop member, the guide track comprising an inclined section extending in the circumferential and longitudinal directions for rotating the rotator relative to the medicament delivery member guard during use, and the stop member comprising a surface facing the distal end of the housing; wherein the rotator comprises a protrusion, the protrusion radially extending relative to the longitudinal axis, and the protrusion comprises a stop surface facing the proximal end of the housing; wherein in the initial unlocked position the protrusion is arranged in the guide track; wherein in the final locked position the rotator is rotated relative to the initial unlocked position, with respect to the position of the medicament delivery member guard; and wherein in the final locked position the surface of the stop member of the medicament delivery member guard abuts the stop surface of the protrusion so as to lock the medicament delivery member guard against being moved distally in relation to the housing.

This safety device can selectively lock the medicament delivery member guard only when a use of the medicament delivery device is completed or interrupted. Such a selective lockout mechanism is achieved by using the rotator to selectively align the locking means, e.g. the protrusion, on the rotational component with a counter locking means, e.g. the stop member, on the medicament delivery member guard, such that accidental lockout before the use of the medicament delivery device is completed or interrupted can be prevented.

Such safety devices can avoid injury by or contamination of a medicament delivery member or damage of the medicament delivery member before, during and after a delivery of a medicament contained in the medicament delivery device.

According to one embodiment, the stop member of the medicament delivery device is closer to the distal end of the housing than the guide track.

According to one embodiment, the rotator may be a generally tubular shape, either extending fully around the circumference or partially around the circumference.

According to one embodiment, the rotator is axially fixed to the housing.

According to one embodiment, the inclined section of the guide track comprises an inclined surface, wherein the protrusion of the rotator comprises an edge, and wherein the edge is engaged with the inclined surface during use.

According to one embodiment, the inclined surface faces towards the distal end of the housing.

According to one embodiment, the inclined surface faces towards the proximal end of the housing.

According to one embodiment, the guide track is a recess or a cut-out.

According to one embodiment, the guide track comprises a ledge.

According to one embodiment, the protrusion comprises a bevelled surface angled towards the distal end of the housing.

According to one embodiment, the rotator comprises a rotator body and a flexible arm; wherein the flexible arm extends from a fixed end to a free end; wherein the fixed end is attached to the rotator body; wherein the free end is radially movable in relation to the longitudinal axis; and wherein the protrusion is arranged on the free end of the flexible arm.

According to one embodiment, the medicament delivery member guard comprises a proximal part and a distal part; and wherein the distal part and the proximal part are axially and rotationally fixed together.

According to one embodiment, the rotator is arranged within the distal part of the medicament delivery member guard; wherein the protrusion is arranged on an outer surface of the rotator; and wherein the guide track and the stop member are arranged on an inner surface of the distal part.

According to one embodiment, the medicament delivery member guard comprises a flange on an outer surface of the medicament delivery member guard; wherein the flange defines the distally directed support surface of the medicament delivery member guard; and wherein the biasing element is arranged between the distally directed support surface of the flange and the proximally directed support surface of the housing.

According to one embodiment, the guide track comprises a linear section extending parallel to the longitudinal axis; and wherein the linear section extends from the inclined section.

According to one embodiment, the stop member of the medicament delivery device is arranged at the distal end of the linear section of the guide track.

According to one embodiment, the linear section extends from the proximal end of the inclined section.

According to one embodiment, the linear section extends from the distal end of the inclined section.

According to one embodiment, the linear section is longer in the longitudinal direction than the inclined section.

According to one embodiment, the medicament delivery device may be an injection device, an inhalation device, a nasal sprayer or an eye drop sprayer.

According to one embodiment, the medicament delivery device comprises a medicament container with a medicament delivery member, the medicament container being arranged in the housing; wherein the medicament delivery member is arranged at the proximal end of the housing, such that the medicament delivery member is covered when the medicament delivery member guard is in the proximal position; and the medicament delivery member is exposed when the medicament delivery member guard is in the distal position.

According to one embodiment, medicament delivery member is integral with the medicament container.

According to one embodiment, medicament delivery member is separate apart from the medicament container and is connectable to the medicament container.

According to one embodiment, medicament delivery member may be a needle or a nozzle.

Generally, all terms used in the claims are to be interpreted according to their ordinary meaning in the technical field, unless explicitly defined otherwise herein. All references to "a/an/the element, apparatus, component, means, etc." are to be interpreted openly as referring to at least one instance of the element, apparatus, component, means, etc., unless explicitly stated otherwise.

BRIEF DESCRIPTION OF THE DRAWINGS

Embodiments of the presently disclosed concept will now be described, by way of example only, with reference to the accompanying drawings, in which:

FIGS. 9A, 9B and 9C show a side view of part of the safety device of FIG. 1 in use.

DETAILED DESCRIPTION

Figure 1:
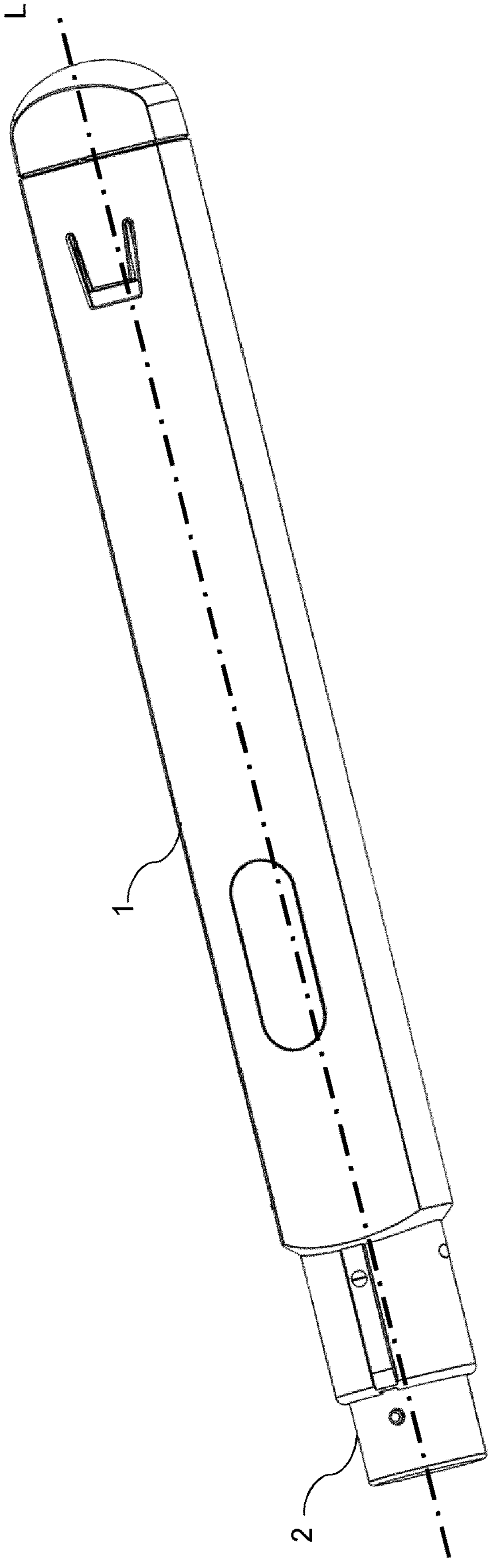
FIG. 1 shows a perspective view of an example of a medicament delivery device including a safety device.

FIGS. 1-10C show a safety device for a medicament delivery device. The safety device comprises a housing 1 extending in a longitudinal direction from a proximal end to a distal end relative to a longitudinal axis L and in a circumferential direction relative to the longitudinal axis L; a medicament delivery member guard 2 arranged within the housing 1, as shown in FIG. 1, and being rotationally fixed and axially movable in relation to the housing 1 along the longitudinal axis L between a proximal position and a distal position; a biasing element 4, as shown in FIG. 2, arranged between a distally directed support surface of the medicament delivery member guard 2 and a proximally directed support surface 11*a* of the housing 1, as shown in FIG. 4A; and a rotator 3 arranged within the housing 1 and being rotatable in relation to the housing 1 between an initial unlocked position and a final locked position, as shown in FIGS. 6A-B. Preferably, the rotator 3 is axially fixed to the housing.

The housing is generally tubular, and may have a circular, triangle or square cross-section, for example, when viewed along the longitudinal direction and with the longitudinal axis L as the centre.

Figure 2A:
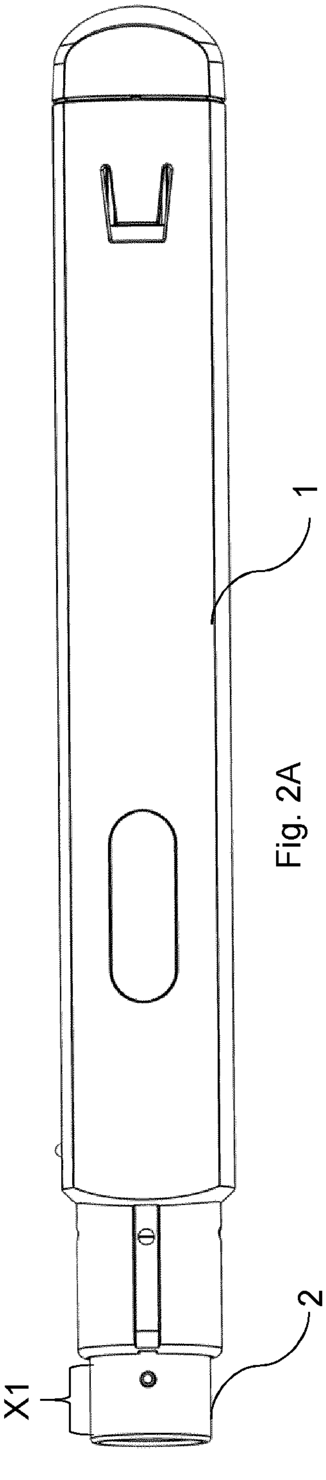
FIGS. 2A, 2B and 2C show a side view of the medicament delivery device of one embodiment in use.
Figure 2B:
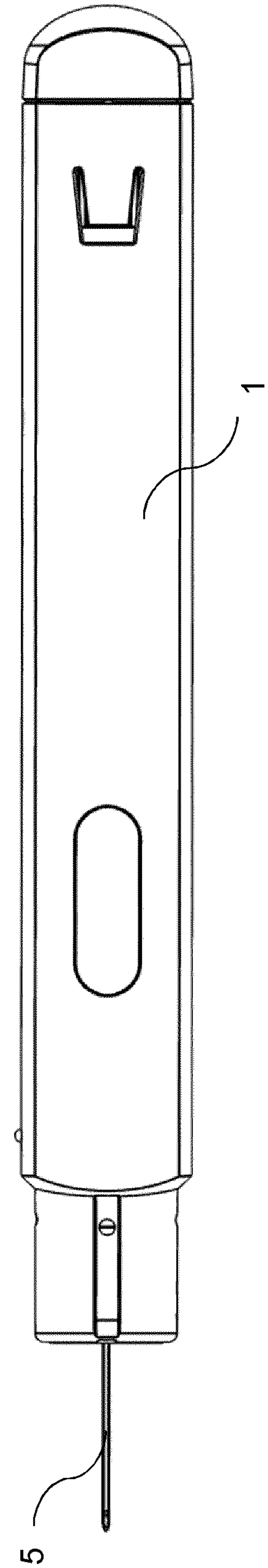
Figure 2C:
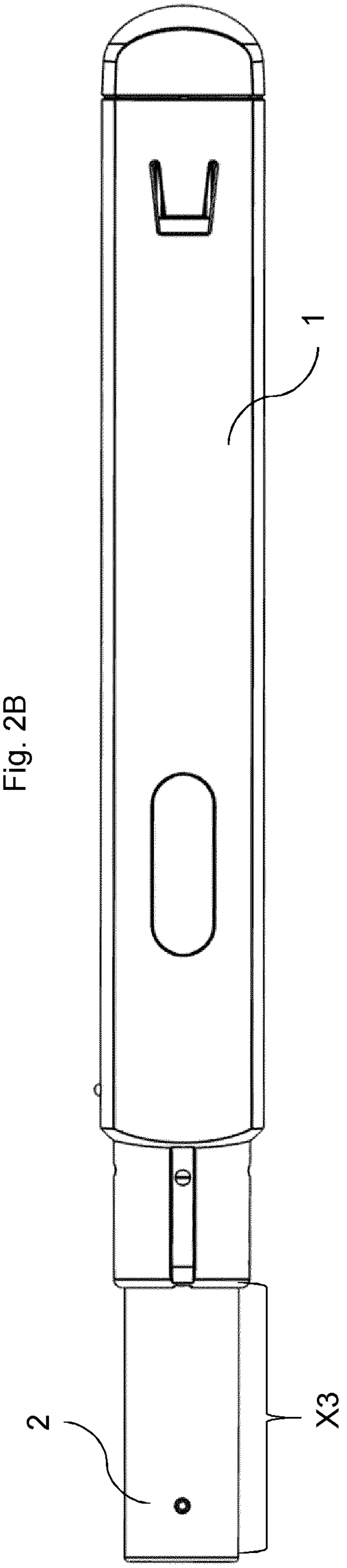

FIGS. 2A-2C illustrate the safety device that is used in a medicament delivery device and the operation sequence. At an initial (before use) position, the proximal portion of the delivery member guard 2 protrudes from the housing 1 with a first length X1 in the proximal position, as shown in FIG. 2A, and protrudes from the housing 1 with a second length (not shown) in the distal position, as shown in FIG. 2B. The first length X1 is greater than the second length, such that when the safety device is used in the medicament delivery device, a medicament delivery member 5 is covered by the medicament delivery member guard 2 when the medicament delivery member guard 2 is in the proximal position; and is exposed when the medicament delivery member guard 2 is in the distal position. In a preferred embodiment as shown in FIG. 2B, the second length may be zero, meaning that the proximal portion of the medicament delivery member guard

2 is completely retracted into the housing 1 when the medicament delivery member guard 2 is in the distal position.

The medicament delivery member guard 2 further comprises a second proximal position, as shown in FIG. 2C. The proximal portion of the delivery member guard 2 protrudes from the housing 1 with a third length X3 when the medicament delivery member guard 2 is in the second proximal position. The third length X3 is greater than the first length X1.

With this design, the safety device can be used in a medicament delivery device with an axially movable medicament delivery member that moves in the proximal direction relative to the housing 1, such as an auto-injector with an auto-penetration function. The medicament delivery member will move further proximally for performing the auto penetration function, so the position of the medicament delivery member in this type of medicament delivery device will end up in a more proximal position than its initial (before use) position. For covering the medicament delivery member both in the initial (before use) position and in the final (after use) position of the medicament delivery member, the medicament delivery member guard of the safety device has a proximal position to cover the medicament delivery member in its initial (before use) position and a second proximal position to cover the medicament delivery member in the more proximal final (after use) position. The mechanism to achieve such an arrangement will be explained in detail later.

Figures 3A, 3B, 3C:
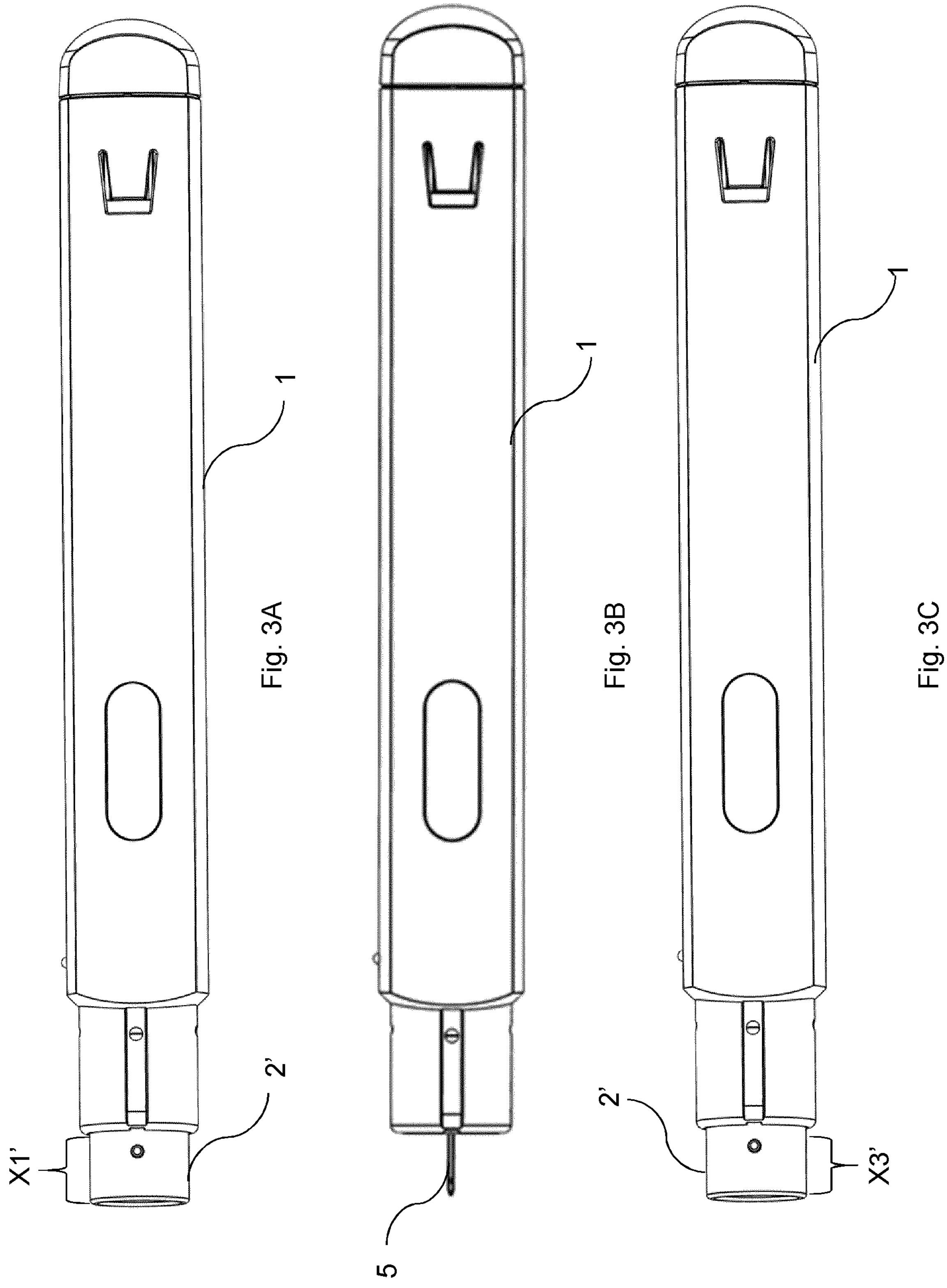
FIGS. 3A, 3B and 3C show a side view of the medicament delivery device of another embodiment in use.

Alternatively, as shown in FIGS. 3A-C, the medicament delivery member guard 2' of the safety device may not protrude any further when in the final position. In this case, the proximal portion of the delivery member guard 2' protrudes from the housing 1 with a first length X1' in the proximal position, as shown in FIG. 3A, then moves to the distal position, as shown in FIG. 3B, so that the medicament delivery device can perform the medicament delivery operation through the medicament delivery member 5. After the medicament delivery device is lifted from the drug delivery site, the medicament delivery member guard 2' moves back to the proximal position, as shown in FIG. 3C, with the medicament delivery member guard 2 protruding from the housing 1 with a length X3' in the proximal position. The length X3 is equal to the first length X1. In this case, the safety device is designed for a medicament delivery device with a medicament delivery member fixed to the housing 1.

Figure 4:
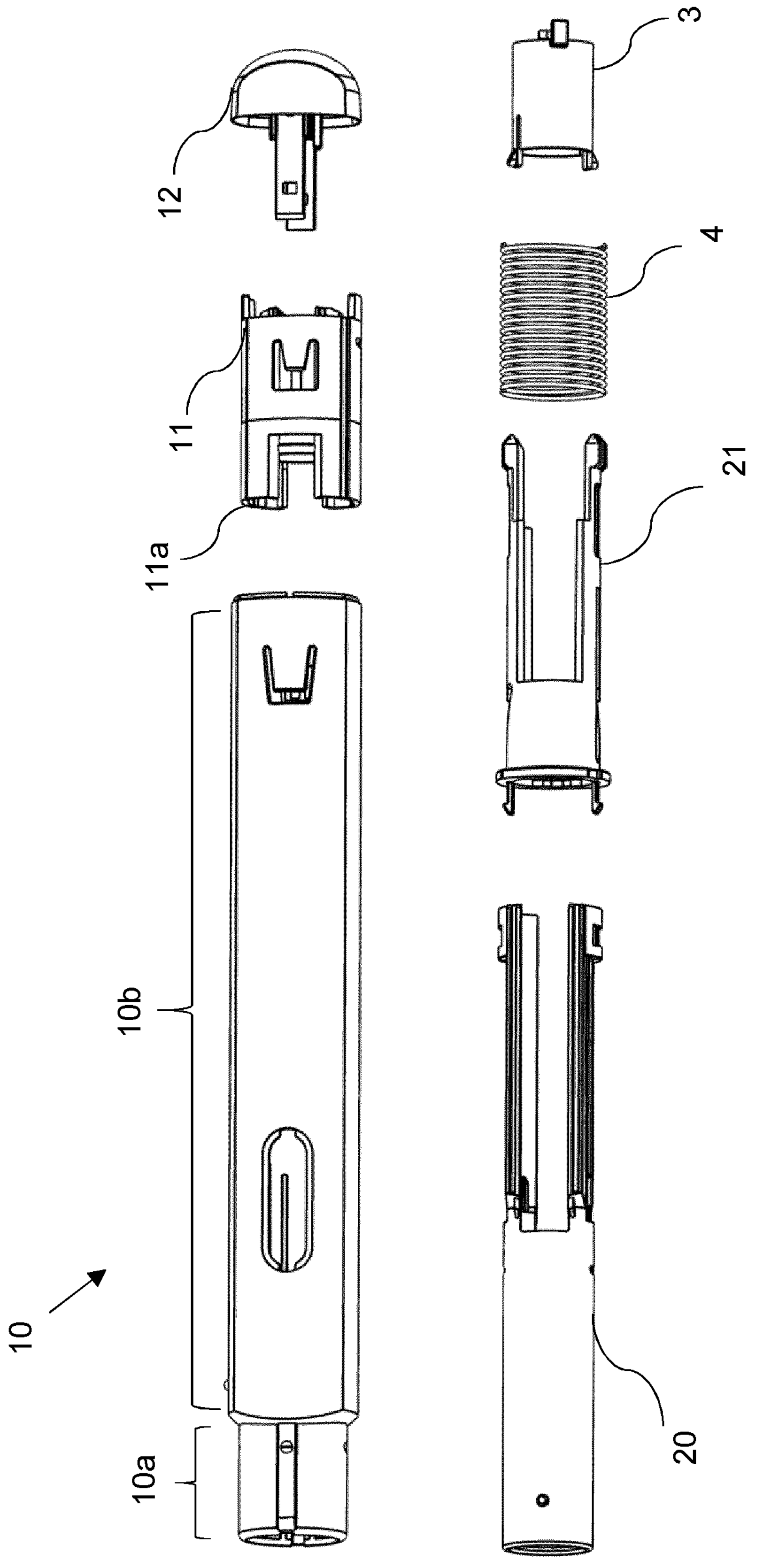
FIG. 4 shows components of the safety device of FIG. 1.

As shown in FIG. 4, an example housing 1 of the safety device comprises an elongated housing shell 10 having an interior space, an inner housing 11 and a rear housing 12. The housing shell 10 comprises a front shell portion 10*a* and a rear shell portion 10*b*. The front shell portion 10*a* comprises an inner diameter that is smaller than an inner diameter of the rear shell portion 10*b*. The rear shell portion 10*b* comprises a proximal part proximally extending to the front shell portion 10*a*. The proximal part has an inner space with a reduced diameter at the proximal end of the proximal part, formed by an inner surface angled relative to the longitudinal axis. A distally directed support surface of the housing 1 is thereby formed on the inner surface of the proximal part of the rear shell portion 10*b*.

It should be noted that, alternatively, the front and rear shell portion 10*a*, 10*b* can also have the same diameter and shape as one another. This depends, for example, on the manufacturing process. The distally directed support surface can be, for example, replaced by a radially extending ledge arranged on the inner surface of the housing shell 10.

The inner housing 11 and the rear housing 12 are axially and rotationally fixed to the housing shell 10 by a fixing element, such as a snap-fit or press-fit. The inner housing 11 is arranged within the housing shell 10 and is arranged at the distal portion of the housing shell 10; the inner housing 11 comprises a proximally directed support surface 11*a* arranged on the proximal end of the inner housing 11. The rear housing 12 is arranged on the distal end of the housing shell 10 and covers the distal opening of the housing shell 10. The medicament delivery member guard 2 of the safety device comprises a proximal part 20 and a distal part 21 axially and rotationally fixed together. The safety device further comprises a rotator 3 and a biasing element 4. The medicament delivery member guard 2, the rotator 3 and the biasing element 4 are all arranged in the interior space of the housing shell 10.

Figure 5A:
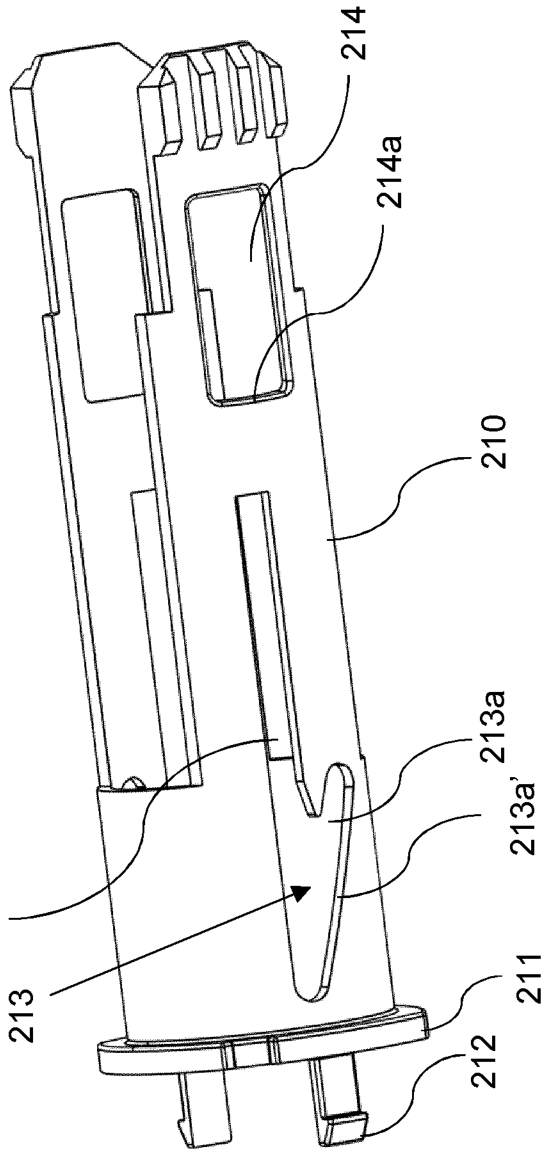
FIGS. 5A-5B show a perspective view of delivery member guard of the safety device of FIG. 1.

The distal part 21 of the medicament delivery member guard 2, as shown in FIG. 5A, comprises an elongated body 210 extending, at least partially, around the longitudinal axis L in a circumferential direction, and extending along the longitudinal axis L; a flange 211 arranged on the proximal end of the body 210, the distal surface of the flange 211 defining the distally directed support surface of the medicament delivery member; and a connector 212 proximally protruding from the proximal end of the body 210, the connector 212 configured to axially and rotationally fix the distal part 21 of the medicament delivery member guard 2 to the proximal part 20 of the medicament delivery member guard 2. The connector can be, for example, a pair of hooks that are able to snap fit into a counter connector 202, shown in FIG. 5B. The distal part 21 of the medicament delivery member guard 2 also comprises a guide track 213 and a stop member 214.

The guide track 213 can, for example, be formed by a recess or cut-out or a radially extending ledge on the elongated body 210 of the distal part 21 of the medicament delivery member 2. The guide track 213 comprises an inclined section 213*a* extending in the circumferential and longitudinal directions on the periphery of the body 210. Preferably, the guide track 213 further comprises a linear section 213*b* arranged on the periphery of the body 210 and parallelly extending relative to the longitudinal axis L, the linear section 213*b* is continued from the inclined section 213*a* or adjacent to inclined section 213. The inclined section 213*a* comprises a distally directed inclined surface 213*a'*.

The stop member 214 is arranged on the distal part 21 of the medicament delivery member guard 2. The stop member 214 can be a cut-out, a ledge or beam that is transversal to the longitudinal axis L. The stop member 214 comprises a surface 214*a* facing the distal end. The surface 214*a* may be a proximal wall of the cut-out, a ledge or a beam, depending on the structure of the stop member 214. The stop member 214 is configured to engage with a counter stop member (this will be explained later in detail) to block the distal axial movement of the medicament delivery member guard when in the final locked position. The stop member 214 is closer to the distal end of the housing 1 than the guide track 213; preferably, the stop member 214 is arranged at the distal end of the linear section 213*b*.

It should be noted that the position of the stop member 214 is designed to lock the medicament delivery guard 2 in the final position with a certain protruding length of the proximal portion of the medicament delivery member guard 2 in relation to the proximal end of the housing 1. The position of the stop member 214 therefore depends on whether the safety device is configured to be used in a medicament delivery device with a medicament delivery member that is axially movable in the proximal direction relative to the housing 1 and the protruding length of the medicament delivery member in the final (after use) position. Similarly, the longitudinal length of the linear section 213*b* in the distal direction depends on whether the safety device is configured to be used in a medicament delivery device with an axially movable medicament delivery member in the proximal direction relative to the housing 1 and the protruding length of the medicament delivery member in the final after used position. The linear section 213*b* is designed to axially guide the protrusion 33 of the rotator (will be explained in detail later) to the stop member 214, the linear section 213*b* is therefore longer in the longitudinal direction than the inclined section 213*a* in the distal direction of the housing 1. The longitudinal length of the linear section 213*b* in the distal direction should be the longitudinal length of the inclined section in the distal direction plus the additional protruding length of the medicament delivery member compared with its original protruding length in relation to the proximal end of the housing 1.

Figure 5B:
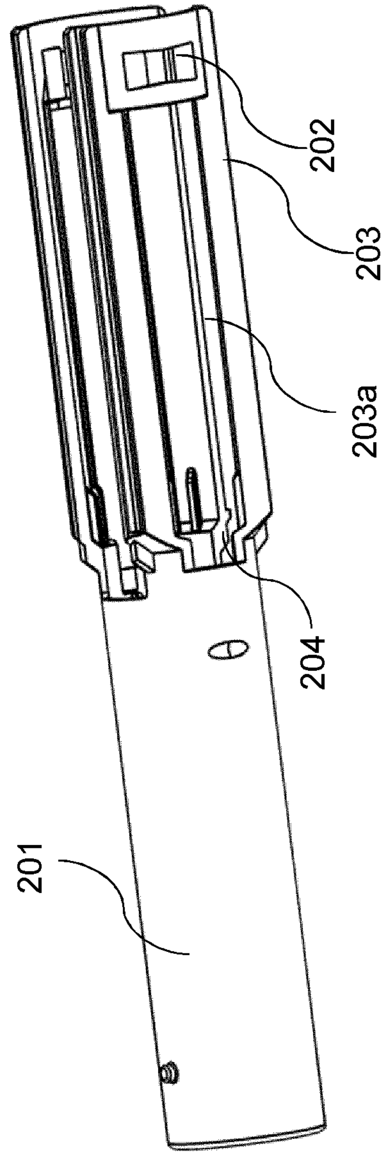

FIG. 5B illustrates the proximal part 20 of the medicament delivery member guard 2. The proximal part 20 of the medicament delivery member guard 2 comprises a sleeve 201. The sleeve 201 is configured to shield a medicament delivery member 5 when the safety device is used in the medicament delivery device. The proximal part 20 of the medicament delivery member guard 2 also comprises the counter connector 202 arranged at the distal portion of the proximal part 20 of the medicament delivery member guard 2. The counter connector 202 is configured to be rotationally and axially fixed with the connector 212 on the distal part 21 of the medicament delivery member guard 2. The shape of the connector 212 and the counter connector 202 are designed to mechanically match with each other and to form a delivery member guard fixing connection in between. Such fixing connection can be a snap-fit, a bayonet fitting or a thread. The proximal part 20 of the medicament delivery member guard 2 further comprises a body portion 203. The body portion 203 comprises a rotational block member 203*a* and a front stop 204. The front stop 204 is configured to abut the distally directed support surface of the housing 1 when the medicament delivery member guard 2 is in the second proximal position.

It should be noted that the front stop 204 of the medicament delivery member guard 2 is configured to abut a counter front stop arranged on an element which is axially immovable in relation to the housing 1 when the medicament delivery member guard 2 is in the second proximal position or the medicament delivery device with the safety device is in the final (after use) position. The medicament delivery member guard 2 is therefore prevented from falling out of the housing 1 under the biasing from the biasing element 4. The distally directed support surface of the housing 1 can alternatively be replaced by a ledge or a distally directed surface arranged on a component of the medicament delivery device, such as a component of the powerpack or medicament container holder, since most of the components of the medicament delivery device are immovable relative to the housing at that time. The front stop can also be alternatively arranged elsewhere, for example on the inner surface of the medicament delivery member guard, depending on the particular arrangement of the counter front stop and on other components of the medicament delivery device. The shape or structure of the front stop and the counter front stop can be varied, but the front stop and the counter front stop should be matched with each other.

Figure 6A:
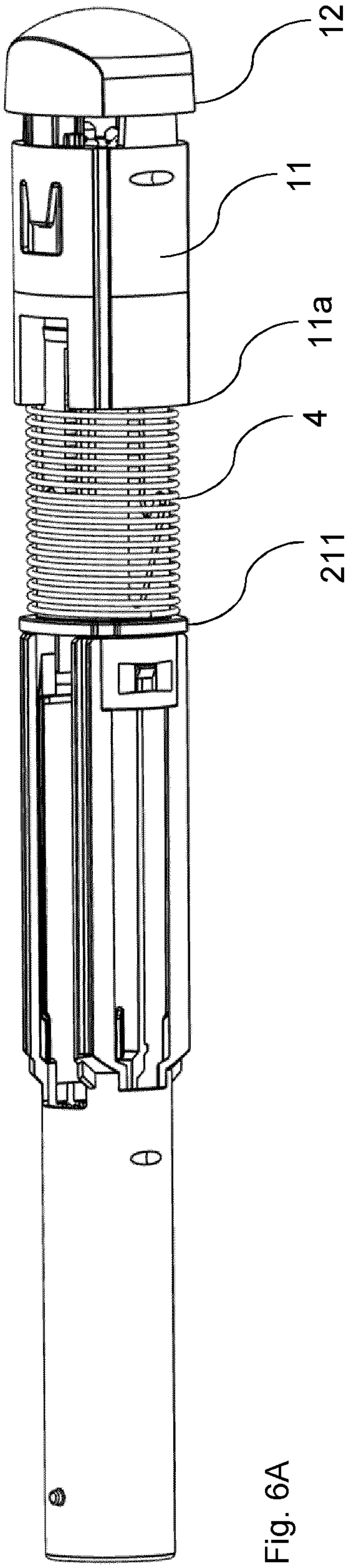
FIG. 6A shows a perspective view of the safety device of FIG. 1.
Figure 6B:
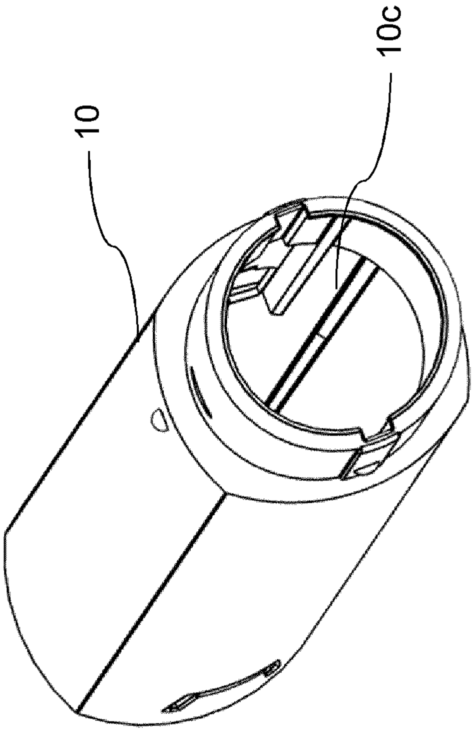
FIG. 6B shows a perspective view of the housing shell of the safety device of FIG. 1.

The rotational block member 203*a* is configured to interact with the counter rotational block member 10*a* arranged on the inner surface of the housing shell 10, as shown in FIG. 6B. The rotational block member 203*a* and the counter rotational block member 10*a* are configured to mechanically match each other, such that when they are assembled together, the medicament delivery member guard and the housing cannot rotate relative to each other. The rotational block member 203*a* and the counter rotational block member 10*a* can be a pair of ribs and grooves, or ribs that are adjacent to each other. Alternatively, the rotational block member 203*a* can also be arranged at the outer surface of the sleeve 201, or the rotational block member 203*a* can even be arranged at the inner surface of the medicament delivery member guard 2. In this case, the counter rotational block member should be arranged at the housing surface of a power pack or a medicament container carrier of the medicament delivery device.

FIG. 6A illustrates the safety device without the housing shell 10. The biasing element 4 has one end that rests on the distally directed support surface of the medicament delivery member, and another end that abuts the proximally directed support surface 11*a* arranged on the proximal end of the inner housing 11. The inner housing 11 is axially and rotationally fixed to the housing shell 10, such that the biasing force of the biasing element 4 can only proximally bias the medicament delivery member to move relative to the housing 1. It should be noted that the proximally directed support surface 11*a* is configured to act as a distal resting surface for engaging with the distal end of the biasing element 4; instead of arranged it on the inner housing 11, it can be replaced by a ledge arranged on the inner surface of the rear housing or the housing shell.

It should be noted that, alternatively, the housing shell 10, the inner housing and the rear housing can be integral as one single housing component; this depends on the manufacturing process. Similarly, the medicament delivery member guard could be a single integral part. The distal part and the proximal part of the medicament delivery member guard can also be a single integral part—for example, the connector and the counter connector can be removed and the medicament delivery member guard can be formed by injection molding directly as one single component that comprises the distal part 21 and the proximal part. Further, instead of providing a flange, multiple discrete ribs can define the distally directed support surface of the medicament delivery member; and instead of being arranged at the distal part of the medicament delivery member guard, the flange can be arranged at the proximal part, preferably arranged at the outer surface of the sleeve 201 of the proximal part. In this case, the biasing element is arranged between the distally directed support surface of the medicament delivery member guard and the proximally directed support surface. The proximally directed support surface is arranged in the proximal portion of the inner surface of the housing shell.

Figure 7C:
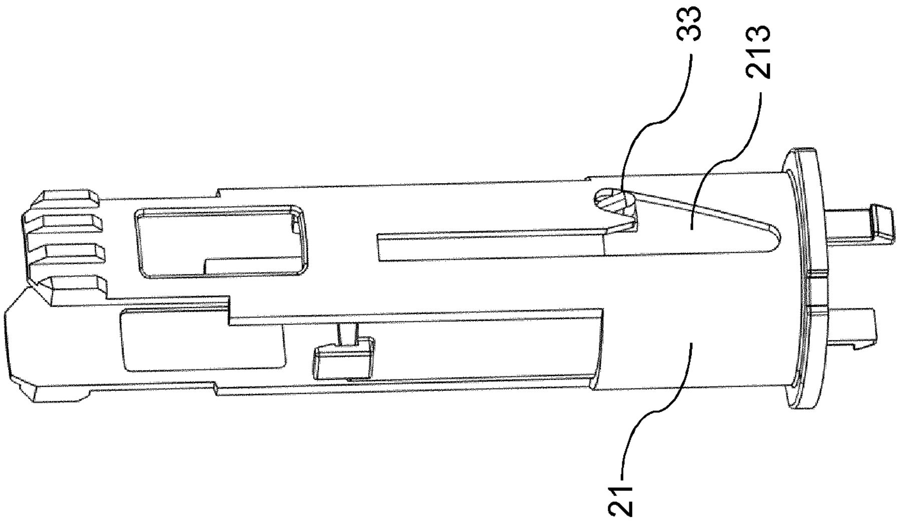
FIGS. 7A, 7B and 7C show a rotator of the safety device of FIG. 1.
Figure 7B:
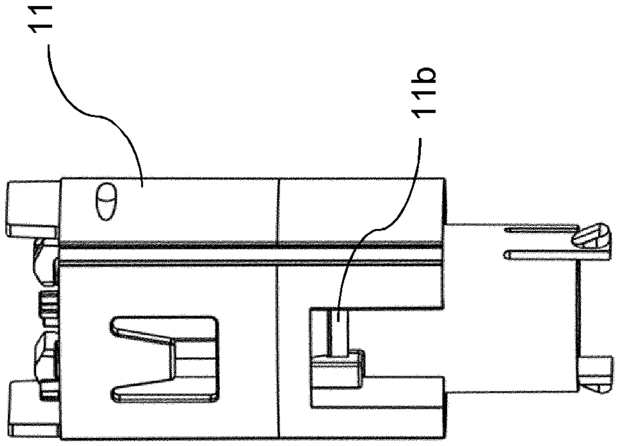
Figure 7A:
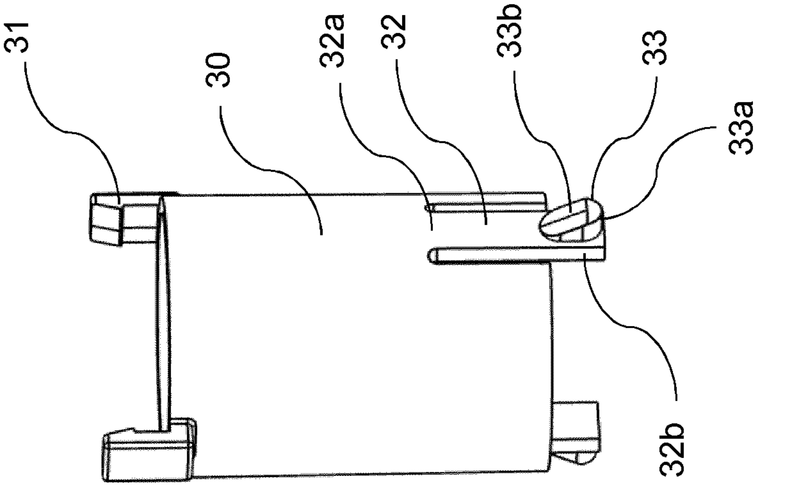

FIG. 7A illustrates the rotator 3 of the safety device. The rotator 3 comprises a rotator body 30, preferably the rotator body is tubular; a rotator connector 31; a flexible arm comprising a fixed end 32*a* attached to the rotator body 30 and a free end 32*b*, the free end 32*b* being radially movable in relation to the longitudinal axis L. The rotator 3 further comprises a protrusion 33, preferably arranged on the free end 32*b* of the flexible arm 32. The protrusion comprises a stop surface 33*a* and a bevelled surface 33*b*. The stop surface 33*a* (which acts as the counter stop member) is configured to engage with the stop member 214 to block the distal axial movement of the medicament delivery member guard 2 when in the final locked position. The bevelled surface 33*b* is angled toward the distal end of the housing 1, since it is a surface angled to the longitudinal axis L and faced toward the distal direction.

As shown in FIG. 7B, in the preferred embodiment, the rotator connector 31 is configured to axially fix the rotator 3 to a counter rotator connector 11*b* on the inner housing 11. Therefore, axial movement of the rotator 3 relative to the inner housing 11 is prevented, but the rotational movement of the rotator relative to the inner housing 11 is allowed. In a preferred embodiment, the rotator connector 31 can be a pair of hooks and the counter rotator connector 11*b* can be a rim or ledge, as shown in FIG. 7B, arranged on the inner housing 11 and radially extending relative to the longitudinal axis L.

The medicament delivery member guard 2 is configured to move between an initial unlocked position and a final locked position. In the initial unlocked position, the medicament delivery member guard 2 is axially movable in relation to the rotator 3 toward the distal direction of the housing 1; in the final locked position, distal axial movement of the medicament delivery member guard 2 in relation to the rotator 3 is prevented. The mechanism will be explained in detail later. The rotator 3 is axially fixed to the housing 1, as described above in the preferred embodiment, the rotator 3 is axially attached to the inner housing 11; the medicament delivery member guard 2 is therefore also locked from moving distally in relation to the housing 1 when it is in the final locked position. The rotator will be rotated when the medicament delivery member guard 2 moves from the initial unlocked position to the final locked position, so that in the final locked position the rotator 3 is rotated relative to the initial unlocked position, with respect to the position of the medicament delivery member guard 2.

The rotator 3 is arranged within the distal part 21 of the medicament delivery member guard 2. The protrusion 33 of the rotator 3 is arranged in the guide track 213 in the initial unlocked position. In a preferred embodiment, the protrusion 33 is arranged in the distal end of the inclined section 213*a* of the guide track 213, as shown in FIG. 7C.

Figures 8A, 8B, 8C:
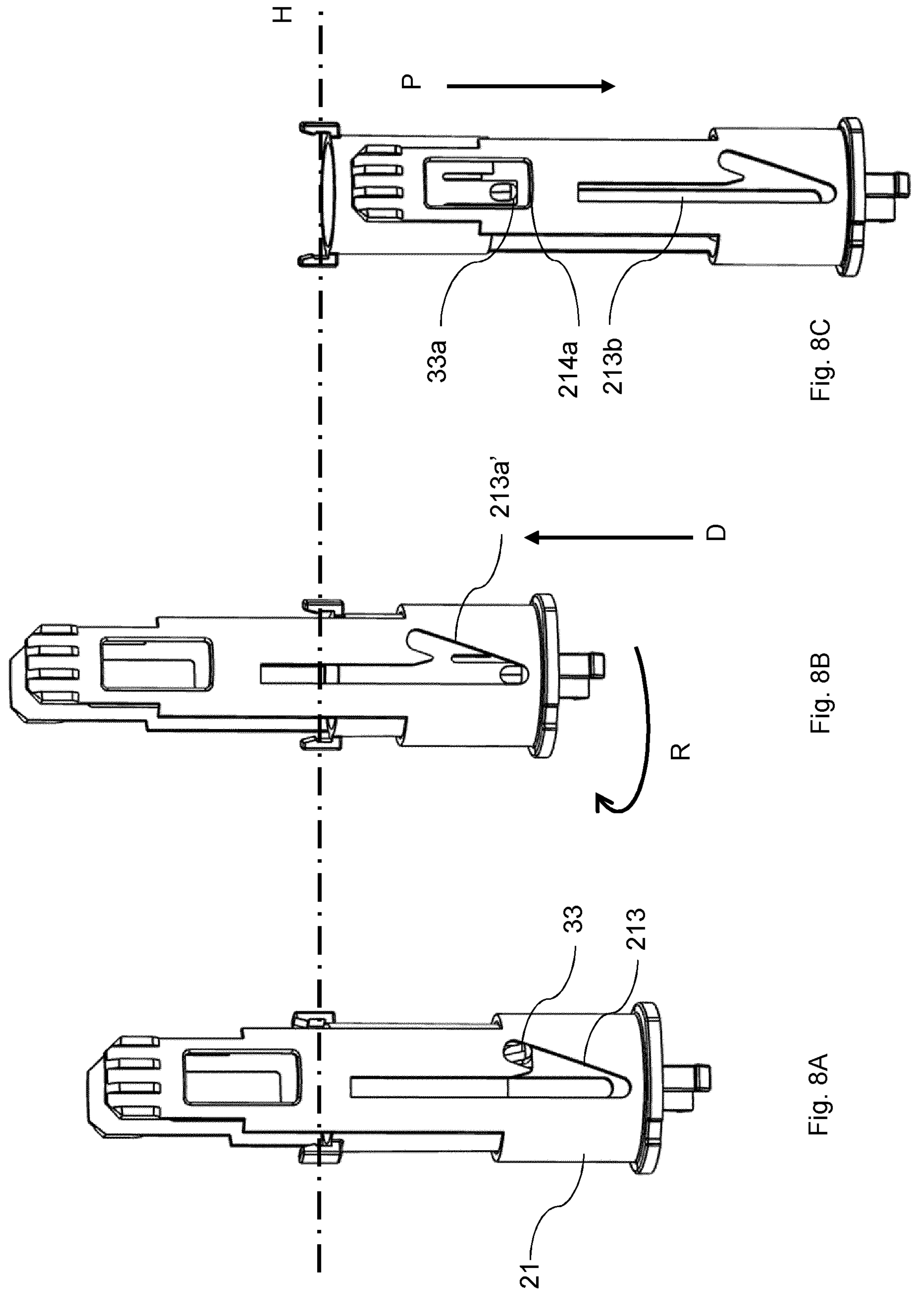
FIGS. 8A, 8B and 8C show a perspective view of part of the safety device of FIG. 1 in use.
Figure 9A:
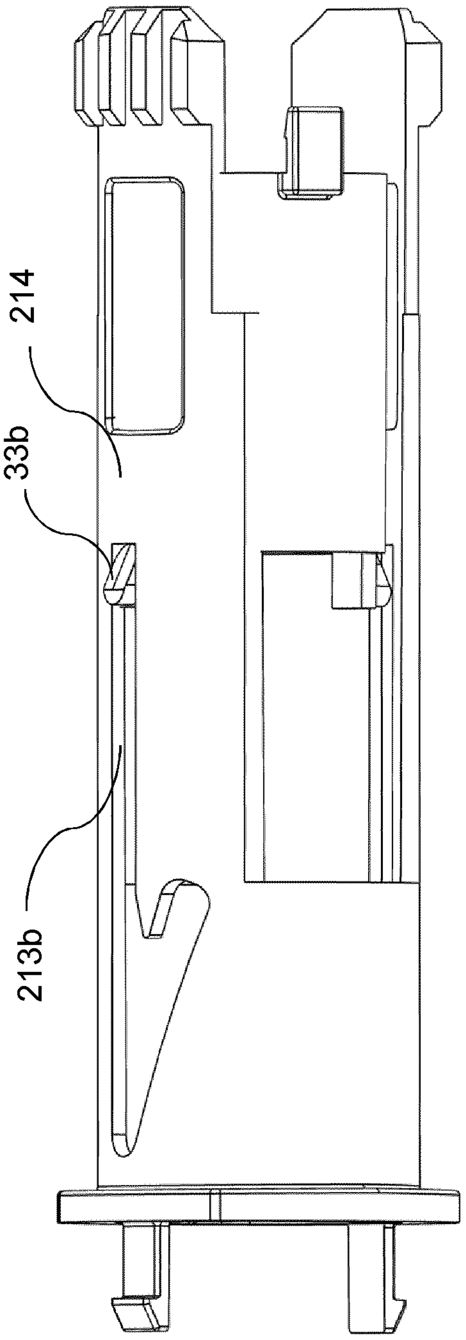
Figure 9B:
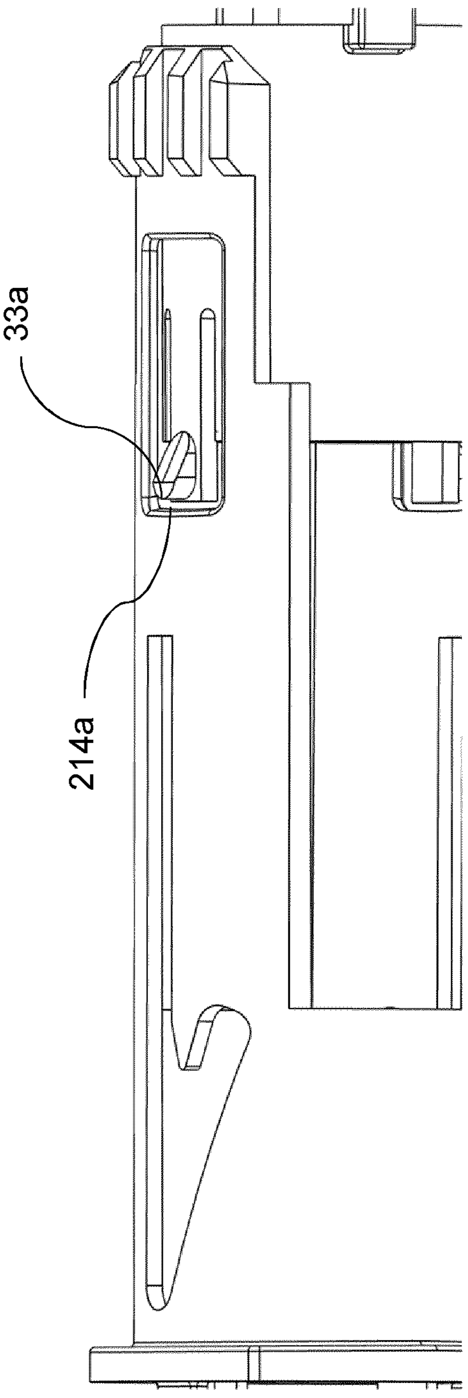

FIGS. 8A-C illustrate the interaction between the distal part 21 of the medicament delivery member guard 2 and the rotator 3 during use. The dashed line H, which is perpendicular to the longitudinal axis, indicates the horizontal position of the rotator 3 in relation to the housin 1.

During use, the medicament delivery member guard 2 is moved to its distal position, as indicated by the arrow D in FIG. 8B. The distal movement of the medicament delivery member guard 2 causes the edge of the protrusion 33 of the rotator 3 to engage with the inclined surface 213*a*' of the inclined section 213*a* of the guide track 213. The rotator 3 is axially locked in relation to the housing 1, e.g. by being axially attached to the inner housing 11 as mentioned above, so the biasing from the inclined surface 213*a*' can only cause the rotator 3 to rotate in relation to the housing 1, as indicated by the arrow R in FIG. 8B. The protrusion 33 travels along the inclined surface 213*a*' with the distal movement of the medicament delivery member guard 2; thereby the rotator 3 is gradually rotated in relation to the housing 1, as shown in FIGS. 8A-8B.

When the medicament delivery member guard 2 reaches its distal position, the protrusion 33 also reaches the proximal end of the inclined section 213*a* of the guide track 213 and is adjacent to the linear section 213*b*, which extends from the proximal end of the inclined section 213*a* in this case, as shown in FIG. 8B. The medicament delivery member guard 2 now is in an intermediate position. In the intermediate position the rotator 3 is rotated relative to the initial unlocked position, with respect to the position of the medicament delivery member guard 2; but the medicament delivery member guard 2 has not yet moved into its final locked position, since the surface 214*a* of the stop member 214 of the medicament delivery member guard 2 is separated apart from the stop surface 33*a* of the protrusion 33.

Once the medicament delivery member guard 2 is moved in the proximal direction in relation to the housing 1, as indicated by the arrow P in FIG. 8C, the linear section 213*b* starts to guide the relative movement between the protrusion 33 of the rotation and the medicament delivery member guard 2. The linear section 213*b* limits the transverse movement of the protrusion 33, such that the rotational movement of the rotator 3 in relation to the medicament delivery member guard 2 is limited. The protrusion 33 of the rotator 3 can be thereby guided in the axial direction towards the stop member. The stop member 214 arranged on the distal part 21 of the medicament delivery member guard 2 moves in the proximal direction in relation to the rotator 3 together with movement in the proximal direction of the medicament delivery member guard 2.

When the proximal end of the stop member 214 moves it comes in contact with the bevelled surface 33*b* of the protrusion 33, as shown in FIG. 8A, since the protrusion 33 is arranged on the free end 32*b* of the rotator 3, and the proximal movement of the stop member 214 causes the stop member 214 to move along the bevelled surface 33*b* of the protrusion 33 and thereby to press the protrusion 33 radially inward. Once the stop member 214 moves past the protrusion 33, the flexible arm 32 flexes back, so that the protrusion 33 of the rotator 3 moves radially outward, and the stop surface 33*a* of the protrusion 33 then faces towards and aligns with the surface 214*a* of the stop member 214, as shown in FIG. 8B. The medicament delivery member guard 2 is therefore moved into the final locked position; and the surface 214*a* of the stop member 214 of the medicament delivery member guard 2 abuts the stop surface 33*a* of the protrusion 33 so as to lock the medicament delivery member guard 2 against being moved distally in relation to the housing 1.

It should be noted that the linear section 213*b* of the guide track 213 is an optional feature for the safety device. The linear section 213*b* of the guide track 213 is configured to secure the linear movement between the medicament delivery member guard 2 and the rotator 3, so that the medicament delivery member guard 2 will not accidentally rotate the rotator 3. However, if the distance between the stop member 214 and the protrusion 33 is short in the intermediate position; or there is a rotational hard stop arranged on the inner surface of the housing 1 or on the counter rotator connector 11*b* of the inner housing 11, the linear section 213*b* of the guide track 213 can be removed from the design.

Figures 10A, 10B, 10C:
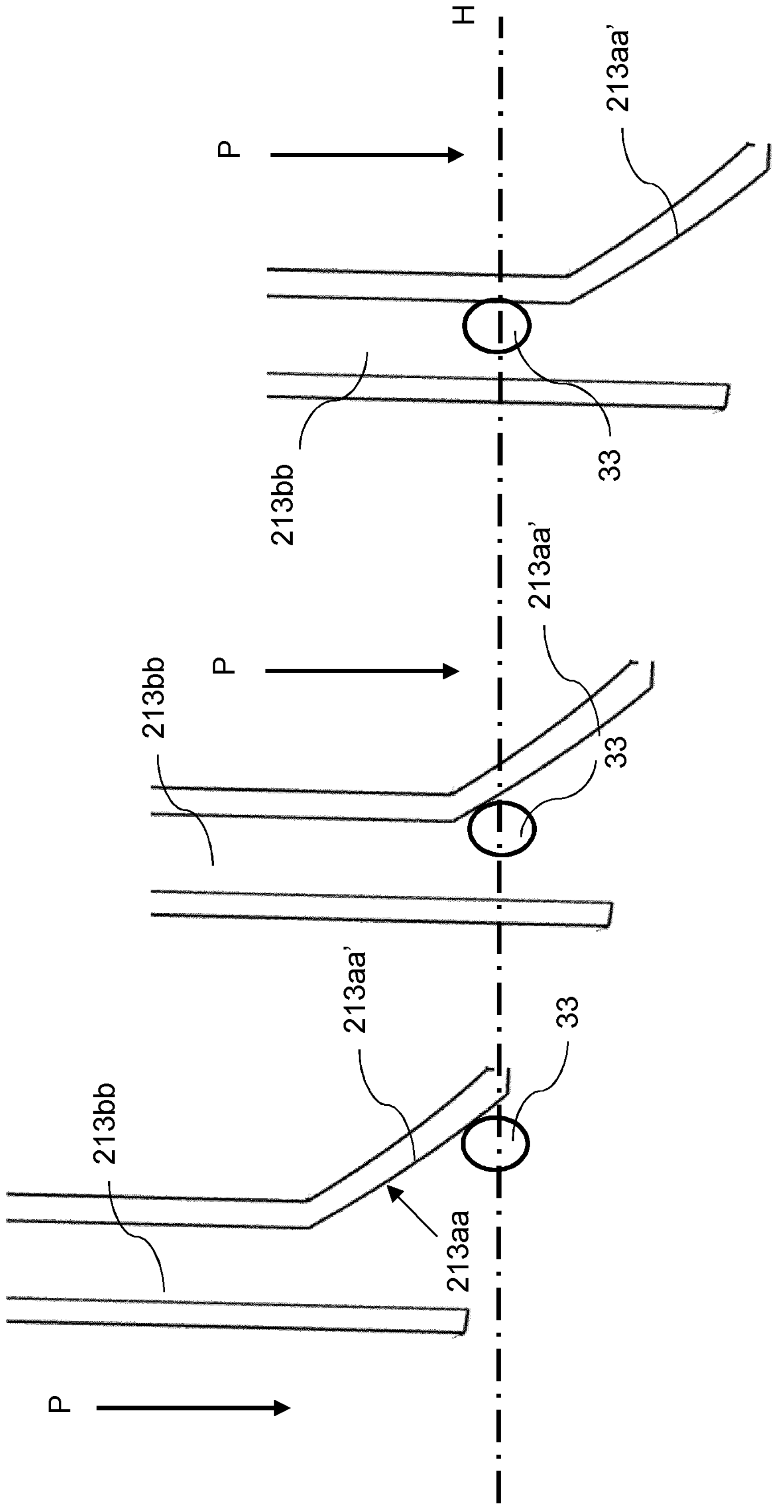
FIGS. 10A, 10B and 10C show a side view of part of the safety device of another embodiment in use.

Also, in an alternative embodiment, as shown in FIGS. 10A-C which show only the outer surface of the body 210 of the distal part 21 of the medicament delivery member guard 2, the inclined surface 213*aa*' of the inclined section 213*aa* of the guide track faces the proximal direction of the housing 1. In this case, the protrusion 33 will move into the inclined section 213*aa* of the guide track when the medicament delivery member guard 2 starts to move in the proximal direction relative to the housing 1 from its distal position, as shown in FIG. 10A, rather than moving into the inclined section immediately upon the medicament delivery guard moving in the distal direction, as in the example described earlier. The edge of the protrusion 33 of the rotator 3 will therefore engage with the inclined surface 213*aa*' of the inclined section 213*aa* of the guide track with the proximal movement of the medicament delivery guard 2 and cause the rotator 3 to rotate, as shown in FIG. 10B. In this case, the stop member 214 can be arranged at the distal end of the inclined section 213*aa*, so that once the rotation of the rotator 3 is completed, the stop member 214 moves past the protrusion and therefore the medicament delivery member guard 2 is moved into the final locked position. The linear section 213*bb* can also be included in this embodiment, such that the linear section 213*bb* extends from the distal end of the inclined section 213*aa*, so that after the rotator 3 rotates, the further proximal movement of the medicament delivery member guard 2 causes the linear section 213*bb* to be adjacent to the protrusion 33 of the rotator, as shown in FIG. 10C. The linear section 213*bb* is configured to guide the protrusion 33 to the stop member 214 as described above.

The distal part 21 of the medicament delivery member guard 2 can alternatively be arranged within the rotator 3 instead of outside the rotator 3 as described above. In this embodiment, the protrusion 33 of the rotator is arranged on the inner surface of the rotator 3; and the guide track 213 and the stop member 214 are arranged on the outer surface of the medicament delivery member guard 2.

Further, in another alternative embodiment, the flexible arm 32 of the rotator 3 may be replaced by a resilient stop member on the distal part 21 of the medicament delivery member guard 2. The stop member 214 can be formed by a resilient material or a resilient structure. Similarly, the bevelled surface 33*b* of the protrusion 33 may be replaced by a bevelled surface facing toward the proximal end of the housing 1 and being arranged on the stop member, e.g. the inner surface of the stop member and is configured to engage with the protrusion 33 of the rotator 3 when in the final locked position.

FIGS. 2A-C illustrate the safety device used in the medicament delivery device. The medicament delivery device comprises a medicament container with the medicament delivery member 5, the medicament container being arranged in the housing 1. The medicament delivery member 5 is axially movable in relation to the housing 1 between an initial (before use) position and a final (after use) position.

When an end user receives the medicament delivery device and plans to use it for delivering the contained medicament, the medicament delivery device will be first in the initial (before use) position, as shown in FIG. 2A, which may be a position where the end user has removed any external packaging and has removed the cap when a cap is provided, and the medicament delivery member guard 2 is in its proximal position and covers the medicament delivery member 5. The relative position of the medicament delivery member guard 2 and the rotator 3 is described by FIG. 8A and the accompanying description. The medicament delivery member guard 2 is held by a holding mechanism via a powerpack of the medicament delivery device or a structure on the inner surface of the housing 1 with the biasing element 4 in a pre-tensioned configuration. Since this aspect does not form part of the present disclosure, and since many different variations of such holding mechanisms can be realised, such as the arrangement disclosed in the cited art, this feature will not be discussed in any further detail herein.

When the end user aims the proximal end of the medicament delivery device to a predetermined medicament delivery site and presses the proximal end of the medicament delivery member guard 2 on the medicament delivery site, the medicament delivery member guard 2 is thereby moved to its distal position, overcoming a force from the biasing element 4. The medicament delivery member 5 is therefore exposed, as shown in FIG. 2B. The relative positions of the medicament delivery member guard 2 and the rotator 3 are shown in FIG. 8B and described in the accompanying description.

After the end of the medicament delivery, the end user lifts the medicament delivery device from the medicament delivery site, and the medicament delivery member guard 2 is therefore biased in the proximal direction under the force from the biasing element 4; and since now the holding mechanism is released due to the firing of the medicament delivery device, the medicament delivery member guard 2 is moved to its second proximal position by the force of biasing element 4 until the front stop 204 abuts the distally directed support surface of the housing 1 and the medicament delivery member 5 is covered, as shown in FIG. 2C. The medicament delivery device is now in its final (after use) position. The relative position of the medicament delivery member guard 2 and the rotator 3 is described in FIG. 8C and the accompanying description.

The present disclosure has mainly been described above with reference to a few examples. However, as is readily appreciated by a person skilled in the art, other embodiments than the ones disclosed above are equally possible within the scope of the present disclosure, as defined by the appended claims.

The invention claimed is:

1. A safety device for a medicament delivery device, the safety device comprising:

- a housing extending in a longitudinal direction from a proximal end to a distal end relative to a longitudinal axis and in a circumferential direction relative to the longitudinal axis;
- a medicament delivery member guard arranged within the housing and being rotationally fixed and axially movable in relation to the housing along the longitudinal axis between a proximal position and a distal position;
- a biasing element arranged between a distally directed support surface of the medicament delivery member guard and a proximally directed support surface of the housing; and
- a rotator arranged within the housing and being rotatable in relation to the housing between an initial unlocked position and a final locked position;
- wherein the medicament delivery member guard comprises a guide track and a stop member, the guide track comprising an inclined section extending in the circumferential and longitudinal directions for rotating the rotator relative to the medicament delivery member guard during use, and the stop member comprising a surface facing the distal end of the housing;
- wherein the rotator comprises a protrusion, the protrusion radially extending relative to the longitudinal axis, and the protrusion comprises a stop surface facing the proximal end of the housing;
- wherein in the initial unlocked position the protrusion is arranged in the guide track;
- wherein in the final locked position the rotator is rotated relative to the initial unlocked position, with respect to the position of the medicament delivery member guard; and
- wherein in the final locked position the surface of the stop member of the medicament delivery member guard abuts the stop surface of the protrusion so as to lock the medicament delivery member guard against being moved distally in relation to the housing.

2. The safety device according to claim 1, wherein the stop member of the medicament delivery device guard is closer to the distal end of the housing than the guide track.

3. The safety device according to claim 1, wherein the inclined section of the guide track comprises an inclined surface, wherein the protrusion of the rotator comprises an edge, and wherein the edge is engaged with the inclined surface during use.

4. The safety device according to claim 3, wherein the inclined surface faces towards the distal end of the housing.

5. The safety device according to claim 3, wherein the inclined surface faces towards the proximal end of the housing.

6. The safety device according to claim 1, wherein the guide track is a recess or a cut-out.

7. The safety device according to claim 1, wherein the guide track comprises a ledge.

8. The safety device according to claim 1, wherein the protrusion comprises a beveled surface angled towards the distal end of the housing.

9. The safety device according to claim 1, wherein the rotator comprises a rotator body and a flexible arm; wherein the flexible arm extends from a fixed end to a free end; wherein the fixed end is attached to the rotator body; wherein the free end is radially movable in relation to the longitudinal axis; and wherein the protrusion is arranged on the free end of the flexible arm.

10. The safety device according to claim 1, wherein the medicament delivery member guard comprises a proximal part and a distal part; and wherein the distal part and the proximal part are axially and rotationally fixed together.

11. The safety device according to claim 10, wherein the rotator is arranged within the distal part of the medicament delivery member guard; wherein the protrusion is arranged on an outer surface of the rotator; and wherein the guide track and the stop member are arranged on an inner surface of the distal part.

12. The safety device according to claim 1, wherein the medicament delivery member guard comprises a flange on an outer surface of the medicament delivery member guard; wherein the flange defines the distally directed support surface of the medicament delivery member guard; and wherein the biasing element is arranged between the distally directed support surface of the flange and the proximally directed support surface of the housing.

13. The safety device according to claim 1, wherein the guide track comprises a linear section extending parallel to the longitudinal axis; and wherein the linear section extends from the inclined section.

14. A medicament delivery device comprising a safety device according to claim 1; wherein the medicament delivery device comprises a medicament container with a medicament delivery member, the medicament container being arranged in the housing; wherein the medicament delivery member is arranged at the proximal end of the housing, such that the medicament delivery member is covered when the medicament delivery member guard is in the proximal position and the medicament delivery member is exposed when the medicament delivery member guard is in the distal position.

15. The medicament delivery device according to claim 14, wherein a linear section of the guide track comprises a linear section is longer in the longitudinal direction than the inclined section.

16. A safety device for a medicament delivery device, the safety device comprising:

a housing having a longitudinal axis;

a medicament delivery member guard rotationally fixed and axially movable inside the housing between a proximal position and a distal position;

a spring operative engaged with a distally directed support surface of the medicament delivery member guard and a proximally directed support surface of the housing; and a rotator rotatably positioned within the housing between an initial unlocked position and a final locked position, wherein the medicament delivery member guard comprises a guide track having an inclined section and a linear section parallel to the longitudinal axis, wherein the rotator comprises a radially extending protrusion having a stop surface slidably positioned in the guide track when the rotator is in the initial unlocked position, wherein axial movement of the medicament delivery member guard causes rotation of the rotator to the final locked position; and wherein when in the final locked position a stop member on the medicament delivery member guard abuts the protrusion so as to lock the medicament delivery member guard against being moved distally relative the housing.

17. The safety device according to claim 16, wherein the stop member on the medicament delivery member guard comprises a surface facing a distal end of the housing that abuts the stop surface of the protrusion when the rotator is in the final locked position.

18. The safety device according to claim 16, wherein the rotator is axially locked in relation to the housing.

19. The safety device according to claim 16, wherein the rotator further comprises a flexible arm having a fixed end and a free end, where the protrusion is arranged on the free end such that protrusion is radially movable in relation to the longitudinal axis.

20. The safety device according to claim 16, wherein the rotator is arranged within a distal part of the medicament delivery member guard and the protrusion is arranged on an outer surface of the rotator such that the guide track and the stop member are arranged on an inner surface of the distal part.

* * * * *